United States Patent [19]

Lormeau et al.

[11] Patent Number: 4,777,161

[45] Date of Patent: Oct. 11, 1988

[54] MEDICAMENTS FAVORING THE PROPERTIES OF BLOOD FLOW AND THEIR USE IN THERAPEUTICS

[75] Inventors: Jean-Claude Lormeau, Maromme; Maurice Petitou; Jean Choay, both of Paris; Francis Toulemonde, Bailly, all of France

[73] Assignee: Choay S.A., Paris, France

[21] Appl. No.: 738,878

[22] Filed: May 29, 1985

[30] Foreign Application Priority Data

May 30, 1984 [FR] France ............................. 84 08570

[51] Int. Cl.⁴ ..................... A61K 31/727; C08B 37/10
[52] U.S. Cl. ...................................... 514/56; 514/822; 536/21

[58] Field of Search ..................... 514/56, 822; 536/21

[56] References Cited

U.S. PATENT DOCUMENTS 4,486,420 12/1984 Lormeau et al. .................... 514/56

FOREIGN PATENT DOCUMENTS 2035349 1/1980 United Kingdom ................. 514/56

Primary Examiner—John Rollins
Attorney, Agent, or Firm—Weiser & Stapler

[57] ABSTRACT

The medicaments of the invention contain in their active principle, oligosaccharides of low molecular weight corresponding to or including heparin fragments.

23 Claims, 1 Drawing Sheet

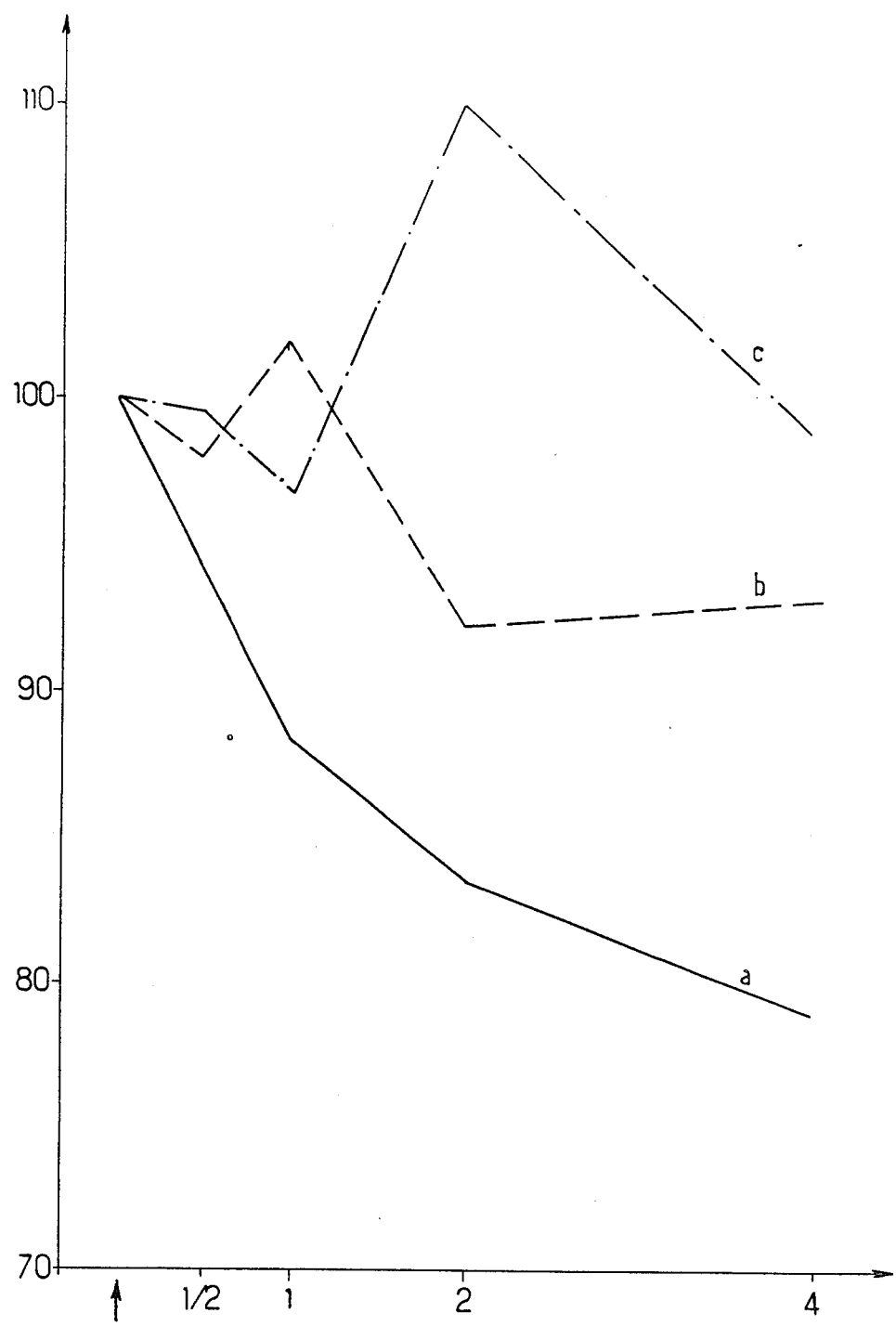

MEDICAMENTS FAVORING THE PROPERTIES OF BLOOD FLOW AND THEIR USE IN THERAPEUTICS

BACKGROUND OF THE INVENTION

The invention relates to medicaments favouring the properties of blood flow and to their use in therapeutics.

This invention constitutes a development of that described in U.S. patent application Ser. No. 204,505 of Nov. 5, 1979, which issued on Sept. 8, 1987 as U.S. Pat. No. 4,692,435, in which medicaments are described containing mucopolysaccharide fractions endowed with biological properties enabling them to play a regulating role with respect to blood clotting, more particularly in the sense of retarding coagulation. This regulatory action is exerted by the bringing into play of inhibitory actions more selective than those of heparin, with respect to a smaller number of factors of coagulation, more particularly of the activated X factor (factor Xa).

These mucopolysaccharides can be obtained by alcoholic fractionation from heparin or from fractions including heparinic constituents as recovered by extraction from animal tissues or organs, in particular of mammals (it will be noted that the term "heparin" is used to denote indifferently a commercial heparin of pharmaceutical grade or a heparin obtained by extraction).

According to their broadest definition, the fractions according to the said US application, are characterised particularly by the following properties they possess a molecular weight of about 2000 to 10,000 daltons;

they are soluble in an aqueous alcohol medium (water-ethanol) having a titer of 55°–61° GL;

they tend to insolubility in a water-alcohol medium having a higher alcohol content;

they are insoluble in pure alcohol;

they possess a ratio of the anti-Xa titer (measured by the Yin-Wessler titer) to the USP titer, of at least 2, particularly at least 3, and even higher than 6.

The inventors have now observed that these fractions exert a powerful action on the rheological behaviour of the blood.

Investigations based on these results have enabled such an action to be demonstrated, generally, in other mucopolysaccharide fractions and compositions corresponding to the above general characteristics.

In the description which follows, these products will also be denoted by the term oligosaccharide.

It is therefore an object of the invention to provide novel medicaments enabling the blood flow to be favoured to an important degree. It is also an object to provide for their use in different administrative forms to counter the factors responsible for blood hyperviscosity.

GENERAL DESCRIPTION OF THE INVENTION

According to the invention there are provided medicaments active on blood viscosity, characterised in that they contain an effective amount of oligosaccharides corresponding to or including heparin fragments of a molecular weight less than 10,000, possessing a ratio of the Yin-Wessler titer to the USP titer of at least 2 and having the above-mentioned solubility properties, or their pharmacologically acceptable salts.

In a preferred family, these medicaments contain at least one mucopolysaccharide fraction according to the principal patent application.

Particularly effective medicaments for the activity concerned comprise mucopolysaccharide fractions having a molecular weight from about 2000 to 8000, particularly of the order of 3500 to 5000.

The NMR spectra ($^{13}$C; radiation of 20 MHz) of solutions of preferred fractions dissolved in deuteriated water show signals having the following characteristics:
- 23.4 ppm: $CH_3$ (NH-acetyl group)
- 54.7 ppm: carbon at the 2 position of glucosamineacetyl units
- 59.2 and 58.8 ppm: carbon at the 2 position of glucosamine sulphate units (the peak in the region of 58 ppm does not appear under identical measuring conditions with heparin)
- 61.7 ppm: carbon at the 6 position with —OH groups
- 67.4 ppm: carbon at the 6 position with —O—sulfate groups
- 98.3 * * ppm: carbon at the 1 position
- 100.00 ppm * *: carbon at the 1 position of sulfated iduronic acid units
- ≅103 ppm: carbon at the 1 position of the glucuronic acid units.

Preferred fractions have a YU/USP ratio of about 3 to 5.

Particularly advantageous medicaments contain a fraction according to Example 1 of said U.S. Ser. No. 204,505.

Such a fraction called below CY 216 possesses a ratio of the Yin-Wessler titer to the USP titer higher than that of heparin of the order of 3.55. It is obtained by alcoholic extraction from heparin.

Others medicaments of this family comprise the fractions obtained by successive alcoholic franctionations followed, as the case may require, by fractionating operations according to the molecular weight such as gel-filtrations or gel-permeations.

The products obtained are characterised by rations of the Yin-Wessler-USP titers higher than 10, particularly of the order of 13 to 16 with Yin-Wessler titers higher than 130 u/mg, particularly of the order of 135 to 160 u/mg.

By purification of these fractions by means of antithrombin III or AT III, according to said US application 204,505, compositions of mucopolysaccharides are obtained whose Yin-Wessler titer at least equal to 300 u/mg, advantageously higher than 1300 u/mg with ratios of the Yin-Wessler titer to the USP titer of at least 6 and which can exceed about 65.

In another preferred family, the medicaments contain oligosaccharides of the type of the mucopolysaccharide compositions described in the U.S. Pat. No. 323,567 on Mar. 20, 1981, which issued on Feb. 19, 1985 as U.S. Pat. No. 4,500,519.

These are compositions possessing more especially a molecular weight of 3000 to 6000 daltons approximately and a Yin-Wessler titer of at least 200 u/mg. These compositions are advantageously obtained by controlled depolymerisation of heparin by means of a chemical agent. The use of nitrous acid, under the conditions reported in said U.S. Pat. No. 4,500,519 results in oligosaccharide chains with terminal units of 2,5-anhydromannose structure. By suitable treatment, these terminal structures are advantageously converted into more stable groups of 2,5-anhydro-mannitol or 2,5-anhydro-mannonic acid structure.

Preferred medicaments of this family contain compositions of the type of those of Example 2 of this U.S. Pat. No. 4,500,519 which terminate in units of 2,5-anhydro-mannitol structure and possess a molecular weight of the order of 2000–2500 daltons.

Compositions of this type, such as obtained by self regulated depolymerisation of heparin by the process described in U.S. patent application Ser. No. 448,639 of Apr. 9, 1982, now abandoned, are also advantageously used for the preparation of the medicaments of the invention.

Other oligosaccharides of low molecular weight with respect to heparin possess also advantageous properties on the blood viscosity.

It is thus with oligosaccharides of the type described in U.S. Pat. No. 4,401,662 granted on Aug. 30, 1983.

Hexasaccharide compositions of great homogeneity of the type described in U.S. Pat. Ser. No. 373,016 of Apr. 29, 1982 now abandoned also have great interest for the development of the medicaments of the invention.

These compositions of structure C'DEFGH obtained by a controlled enzymatic depolymerisation process possess particularly Yin-Wessler titers higher than 2000 u/mg and USP or APTT titers of the order of 10 or less.

In another preferred family of medicaments of the invention, the oligosaccharides of low molecular weights are constituted by the products described in the patent application Ser. No. 457,931 of Jan. 14, 1983 now abandoned. These products obtained by a synthesis route possess a higher degree of purity and can include considering their method of production the desired substituents facilitating a given effect. In general, these oligosaccharides possess the structure of fragments of heparin or heparane sulfate or are constituted by such fragments with alternate amino-sugar-uronic acid units (or structural analogs) or the reverse.

Among the products described, will be mentioned the pentasaccharide of structure DEFGH and bearing the number 50 of formula:

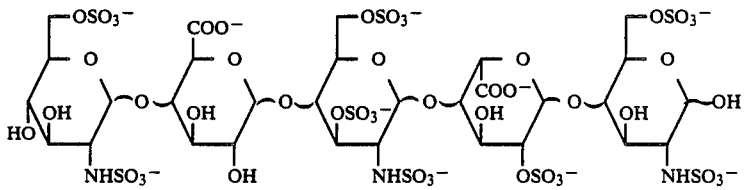

These oligosaccharides are characterised particularly by the fact that they do not contain more than 8 saccharide units, that they possess a specific affinity for ATIII and a ratio of the Yin-Wessler titer to the USP titer of at least 30.

The USP activity observed is practically nil whilst the Yin-Wessler titer can exceed by ten times that of heparin and even reach a value of about 2000 u/mg with an octosaccharide called ABCDEFGH obtained by enzymatic depolymerisation, of the structure:

Other oligosaccharides which are revealed to be valuable for developing medicaments of the invention correspond to those described in U.S. application filed under the priority of FR NO 84 07589 of May 16, 1984.

According to their broadest definition, said oligosaccharides comprise from 4 to 12 units selected from

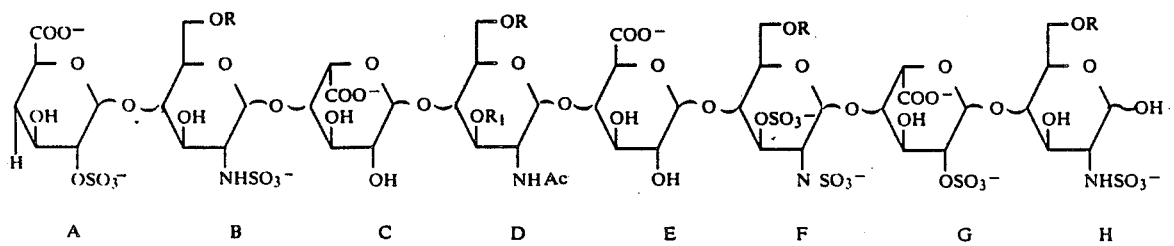

among amino sugar and uronic acid units, or the converse, and that they contain a tetrasaccharide enchainment of the structure DEFG corresponding to the formula:

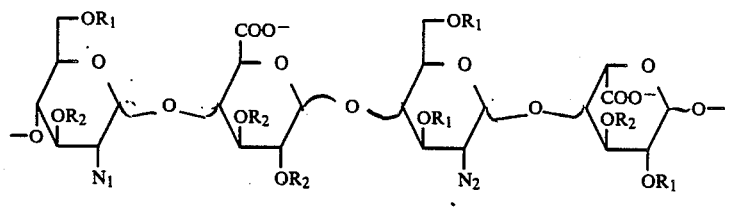

in which:
the radicals $R_1$, identical or different from one another, represent an inorganic anion in particular, a sulfate group or phosphate group,
$R_2$ has one of the meanings given for $R_1$ or represents a hydrogen atom,
$N_1$ and $N_2$, identical or different from one another, represent a functional amine group, in particular in the form of a salt with an inorganic anion such as defined above, or substituted by an acyl group —$COR_3$ where $R_3$ represents an alkyl radical and their salts.

A preferred oligosaccharide of said family has the following formula:

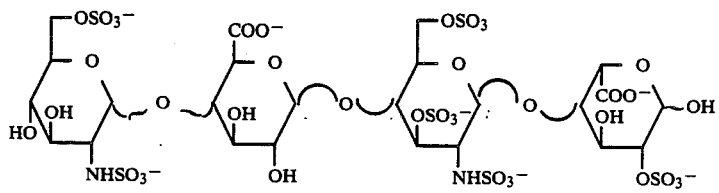

In a modification of the invention, the oligosaccharide employed in the various families of medicaments mentioned above are used in the forms of conjugates with ATIII united by a covalent linkage or, as described in U.S. patent application Ser. No. 626,305 of July 1, 1984, in the form of complexes resulting from the affinity of these oligosaccharides for ATIII.

As already emplasised, these oligosaccharides of low molecular wieght exert an action of great interest on the rheological behaviour of the blood, considerably reducing the blood viscosity.

These properties permit their use in various hyperviscosity syndromes where until now reliance was placed essentially on techniques of hemodilution of short-term effects.

The hyperviscosity syndromes associated with a certain number of diseases will be mentioned in particular arteriopathies chronic cerebral insufficiencies in elderly patients, hyperviscosity problems encountered in burn patients, hyperviscosity syndromes associated with conditions of sub-acute arterial insufficiency, for example, in the case of cerebral ischemia (localised thromboses in the brain) cardiac insufficiency (condition of anginal pain).

The study of the action of these medicaments has shown, in another aspect that they permit the risks of demineralisation encountered in a long term treatment to be avoided, for example in the case of pregnant women or of thrombo-embolic patients reacting badly to oral anticoagulants and placed for this reason under long term treatment with heparin.

The above oligosaccharides are associated with the usual pharmaceutical excipients. The good absorption of these oligosaccharides by the mucus membranes of the intestinal passage enables their use in numerous galenic forms.

The invention relates, in particular, to medicaments in which the vehicle is suitable for oral administration. Corresponding administrative forms comprise, tablets, capsules, dragees, granulates, pills and the like. Administration in the form of liposomes of various oligosaccharides of low molecular weights mentioned above has proved to be particularly suitable for the treatment of hyperviscosity syndromes.

Other pharmaceutical compositions comprise these oligosaccharides in association with suitable excipients for rectal administration. Corresponding administrative forms are constituted by suppositories. In particular, the invention relates also to injectable, sterile or sterilisable pharmaceutical compositions, for intravenous, intramuscular or subcutaneous administration.

In generaly, administration of 3 to 10 times $10^3$ anti-Xa u (Yin-Wessler), particularly of the order of $5 \times 10^3$ anti-Xa u approximately two or three times daily appears satisfactory.

These posologies will however be adapted according to the condition of the patient. Considering the complete inocuousness of these products, larger doses may be administered without troublesome effect.

In order to illustrate the invention, there are reported in the example which follows, the results obtained on healthy volunteers to which medicaments containing oligosaccharides as defined above have been administered.

FIG. 1 includes graphs of the variation of the viscosity of the whole blood of subjects as a function of time after administration of physiological serum, heparin and a medicament of the invention.

EXAMPLE:

Study of the effect of a medicament containing CY 216 on the viscosity of the blood on subjects in good health The results which follow relating to this study concern 6 subjects in good health to which were administered, intravenously, after fasting overnight, at an interval of one week, 70 anti-Xa units/kg of CY 216, of heparin, and then of an equivalent volume of physiological serum.

Prior to the administration of the medicaments, and then 30, 120 and 240 min after this administration, blood specimens were taken and the viscosity determined at 5 different shearing speeds by means of a conventional rotary viscosimeter.

The results obtained are reported in FIG. I in which the curves (a) to (c) correspond respectively to measurements carried out in the case of the administration of CY 216, heparin and physiological serum.

The examination of this figure shows an important reduction in the viscosity of the total blood on the administration of CY 216, demonstrating the effectiveness of this product on the flow properties of the blood.

Considerable reductions in the viscosity of the blood have also been observed by using in place of CY 216, oligosaccharides of low molecular weight obtained by nitrous or enzymatic depolymerisation such as the product denoted above by CY 222 or again octosaccharides of the type ABCDEFGH and hexasaccharides of the type CDEFGH.

In the same way, the products obtained synthetically such as the pentasaccharide of the type DEFGH, the tetrasaccharide of the type DEFG or other oligosaccharides containing at least one disaccharide sequence of the above octasaccharide A-H have shown great effectiveness.

Other tests have been carried out on patients suffering from vascular diseases. The administration of oligosaccharides at the dosage of 100 units anti-Xa/kg thrice daily during a month have permitted the condition of these patients to be favourably modified.

We claim:

1. A therapeutic method for treatment of whole blood hyperviscosity symptoms of a patient in need thereof which comprises administering to said patient a biological composition which comprises a therapeutically acceptable carrier and a quantity of heparinic oligosaccharide fractions or the physiologically acceptable salts thereof, which oligosaccharides have (1) a molecular weight less than 10,000 daltons, (2) a ratio of anti-Xa titer to USP titer of at least 2, (3) are soluble in water-alcohol having a titer of 55°-61° GL, but tend to insolubility in a water-alcohol medium having a higher alcohol content and (4) are insoluble in pure alcohol, wherein said quantity of oligosaccharide fractions is sufficient to affect the blood rheology by lowering the blood viscosity, determined by taking patient blood sample viscosity measurements periodically for about four hours after administration.

2. The method of claim 1, wherein said lowering of viscosity is at least an improvement of 12.7% of that obtained with heparin after one hour under comparable conditions.

3. The method of claim 2, wherein said lowering of viscosity is at least an improvement of 13.0% of that obtained with heparin after four hours under comparable conditions.

4. The method of claim 1 wherein said lowering of viscosity is already measurable about one hour after administration and is at least an improvement of 12.7% of that obtained with heparin under comparable conditions.

5. The therapeutic method of claim 1 wherein the amount of heparinic oligosaccharide fraction administered is between 3,000 and 10,000 anti-Xa units.

6. The therapeutic method of claim 5 wherein the amount of heparinic oligosaccharide fraction administered is 5,000 anti-Xa units.

7. The therapeutic method of claim 1, wherein the composition is administered at least twice a day.

8. The therapeutic method of claim 7 wherein the composition is administered three times a day.

9. The therapeutic method of claim 1 wherein the amount of heparinic oligosaccharide fraction administered is 100 anti-Xa units per kilogram of patient weight.

10. The therapeutic method of claim 9 wherein the fraction is administered twice daily for a period of one month.

11. The therapeutic method of claim 1 wherein the administration of the composition is by oral ingestion.

12. The therapeutic method of claim 11 wherein the administrative form is selected from the group consisting of tablets, capsules, dragees, granulates and pills.

13. The therapeutic method of claim 1 wherein the administration of the composition is by rectal suppository.

14. The therapeutic method of claim 1 wherein the administration of the composition is by injection or infusion.

15. The therapeutic method of claim 1 wherein the patient is an elderly patient.

16. The therapeutic method of claim 1 wherein the patient has burns.

17. The method of claim 1, wherein the oligosaccharides have a molecular weight from about 2,000 to about 9,000 daltons.

18. The method of claim 17, wherein the oligosaccharides have a molecular weight from about 3,500 to 5,000 daltons.

19. The method of claim 1, wherein the oligosaccharides have a ratio of anti-Xa titer to USP titer of 3.55.

20. The method of claim 1, wherein the oligosaccaride is an octosaccharide with a ratio of anti-Xa titer to USP titer of at least 30.

21. The method of claim 1, wherein the oligosaccharide has a molecular weight in the range of about 2,000 to 2,500 daltons and comprises 2,5-anhydromanno terminal units.

22. The method of claim 1, wherein the oligosaccharide is a pentasaccharide of the formula:

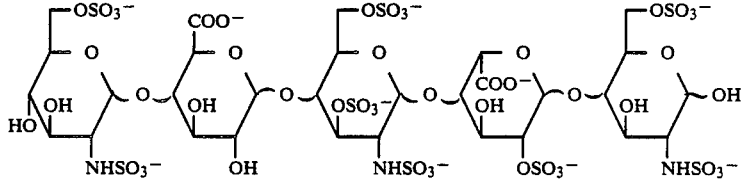

23. The method of claim 1, wherein the oligosaccharide is a tetrasaccharide of the formula:

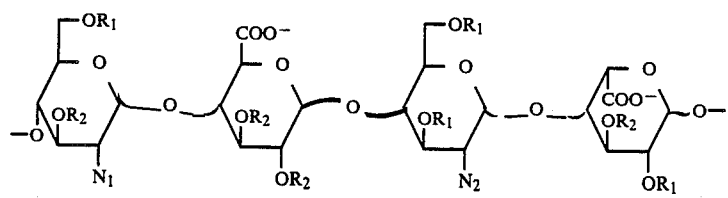

wherein the radicals $R_1$ may be the same or different and are selected from the group consisting of sulfate and phosphate, $R_2$ may be hydrogen or the same as $R_1$ above and $N_1$ and $N_2$ may be the same or different, and are selected from the group consisting of an amino group, an amino group substituted by a sulfate or phosphate group, or an amino group substituted by an acyl group, $-COR_3$, wherein $R_3$ is alkyl radical.

* * * * *